United States Patent [19] [11] 4,312,863
Gold et al. [45] Jan. 26, 1982

[54] TREATMENT OF GLAUCOMA

[75] Inventors: Elijah H. Gold, West Orange; Wei Chang, Livingston, both of N.J.

[73] Assignee: Schering Corporation, Kenilworth, N.J.

[21] Appl. No.: 174,988

[22] Filed: Aug. 4, 1980

Related U.S. Application Data

[63] Continuation-in-part of Ser. No. 137,935, Apr. 7, 1980, which is a continuation-in-part of Ser. No. 89,077, Oct. 29, 1979, abandoned, which is a continuation-in-part of Ser. No. 944,516, Sep. 20, 1978, abandoned.

[30] Foreign Application Priority Data

Sep. 13, 1979 [ZA] South Africa ..................... 79/4872

[51] Int. Cl.³ .................... A61K 31/60; A61K 31/165
[52] U.S. Cl. .................................... 424/230; 424/324
[58] Field of Search ............................... 424/230, 324

[56] References Cited

U.S. PATENT DOCUMENTS 4,012,444  3/1977  Lunt ............................. 424/324 X
4,127,674  11/1978  Leopold ........................... 424/324
4,173,583  11/1979  Gold ............................. 260/559 S

FOREIGN PATENT DOCUMENTS 2616403  10/1976  Fed. Rep. of Germany ...... 424/324

OTHER PUBLICATIONS

Elliot et al., Brit. J. Ophthal., vol. 59, 1975, pp. 296–300.
Pau, Klin. Monatsble Angenheilkd, vol. 126, 1955, pp. 171–176.
Rutkowski et al., Trans. Am. Ophth. & Otol., vol. 77, 1973, pp. 137–142.
Mullen et al., Arch. Ophthalmal., vol. 46, 1951, pp. 549–552.
Langham, et al. Exp. Eye Res., vol. 15, 1973, pp. 75–84.
Leopold, (Modell, Ed.) Drugs of Choice, 1978–1979, 1979, pp. 664–675.
Hagedorn et al., Lancet, Apr. 20, 1974 p. 773.
Vale et al., Brit. J. Ophthal. vol. 56, 1972, pp. 770–775.
British Med. J., Jan. 24, 1976, pp. 180–181.
Murray, Arch. Ophthalmol. vol. 97, No. 4, 1979, pp. 723–726.

Primary Examiner—Anna P. Fagelson
Attorney, Agent, or Firm—Gerald S. Rosen; Mary S. King; Barbara L. Renda

[57] ABSTRACT

Ophthalmic compositions containing (−)-5-{(R)-1-Hydroxy-2[(R)-1-methyl-3-phenylpropyl)amino]ethyl}salicylamide and a method of using them in the treatment of glaucoma are disclosed.

4 Claims, No Drawings

TREATMENT OF GLAUCOMA

This application is a continuation-in-part of our copending application Ser. No. 137,935, filed Apr. 7, 1980, which is a continuation-in-part of our copending application Ser. No. 89,077, filed Oct. 29, 1979, now abandoned which in turn is a continuation-in-part of our application Ser. No. 944,516, filed Sept. 20, 1978, now abandoned, the disclosures of which are hereby incorporated by reference.

BACKGROUND OF THE INVENTION

Glaucoma is a condition of the eye characterized by increased intraocular pressure. Untreated, the condition eventually leads to irreversible retinal damage and blindness. Presently drugs such as pilocarpine and its various salts are used for its treatment. Although these drugs are useful they generally exhibit side effects such as extreme miosis, spasm of accomodation, night blindness and transient blurred vision. It has now been found that the R,R-stereoisomer of labetalol or a pharmaceutically acceptable salt thereof is effective in reducing intraocular pressure without the side effects associated with pilocarpine type drugs.

DETAILED DESCRIPTION OF THE INVENTION

The present invention relates to a method of treating glaucoma and ocular hypertension by applying an effective amount of the R,R-stereoisomer of labetalol or a pharmaceutically acceptable salt thereof to the human or animal eye suffering from glaucoma or ocular hypertension. The invention also relates to a method of reducing normal intraocular pressure. The invention further relates to ophthalmic compositions comprising this compound.

It is a purpose of this invention to provide a novel antiglaucoma composition as well as a method of reducing intraocular pressure which partially or totally eliminates one or more of the above-mentioned side effects. The active compound of this composition is a stereoisomer or a pharmaceutically acceptable salt thereof, of one of the diastereomers of the compound labetalol which is described in Lunts, et. al., U.S. Pat. No. 4,012,444. Chemically, this isomer is (−)-5-{(R)-1-hydroxy-2-[(R)-1-(1-methyl-3-phenyl-propyl)amino]ethyl}salicylamide (hereinafter for convenience referred to as the R,R-stereoisomer).

Whereas the foregoing Lunts, et. al. patent recognizes that compounds such as labetalol have optically active forms, no example of an optically active form is given. The subject stereoisomer, or indeed any of the stereoisomers of labetalol, has, heretofore, been unknown in the art.

Labetalol has been characterized as a "new kind of anti-hypertensive" since it has the effect of having $\beta$-blocking activity as well as blockade of $\alpha$-adrenoceptors in the peripheral arterioles. Its major side-effect, postural hypotension, is attributable to its $\alpha$-blocking activity. Other symptoms associated with $\alpha$-blockade, e.g., dizziness and failure of ejaculation are also observable. See, for instance, Scrip, p. 20, Apr. 2, 1977.

The unique pharmacological profile of labetalol and its use as an antihypertensive agent are suggested to be largely a function of the exquisite balance of its $\alpha$- and $\beta$-adrenergic blocking activities. As disclosed in the file history of the aforesaid Lunts, et. al. patent, even slight changes in the chemical structure of labetalol deleteriously affect this ratio, and even in those few variants where the ratio is unchanged, the absolute potencies of these variants are taught to be too low to be useful as antihypertensive agents.

The subject R,R-stereoisomer exhibits, as compared to labetalol, a totally distinct pharmacological profile. For instance, it possesses a high increase in $\beta$-adrenergic blocking potency, yet a decrease in the $\alpha$-adrenergic blocking potency. The $\alpha$- and $\beta$-blocking activities may be determined by the methods described in Farmer et. al., *Brit. J. Pharm.*, 45, 660 (1972); Robson, *J. Pharm. Exp. Therap.*, 175, 157 (1970); and Levy, *Arch. Int. Pharmacodyn. Ther.*, 204, 143 (1973). Thus, the $\beta$: $\alpha$ ratio of the R,R-stereoisomer is markedly higher than the ratio of labetalol. These ratio potency changes could not have been predicted on a theoretical basis and they give the R,R-stereoisomer a significantly different $\beta/\alpha$-blocking ratio from that of the parent labetalol.

Additionally, the R,R-stereoisomer possesses much increased direct vasodilatory activity over that of labetalol. The overall pharmacological profile of the R,R-stereoisomer is thus that of vasodilating-$\beta$-blocker.

One of the two diastereomers of labetalol has been taught to possess interesting antiarrhythmic properties for individuals who have suffered myocardial infarctions (see Belgian Pat. No. 840,779 and U.S. Pat. No. 4,173,583). This diastereomer, called A, is identified as the one whose hydrochloride salt has the higher melting point (identified as Isomer 1 in U.S. Pat. No. 4,012,444). The R,R-stereoisomer of this application is derived from diastereomer B.

U.S. Pat. No. 4,127,674 (1978) teaches the use of labetalol and several close structural analogs thereof for reducing intraocular pressure and alleviating the symptoms of glaucoma. Murray, et. al., *Arch. Opthalmol.* 723–26, (1979) also discloses such activity for labetalol.

Most surprisingly, we have found that the R,R-stereoisomer possesses greater potency when used to lower intraocular pressure than its parent compound labetalol. Additionally, it has been found to affect only the treated eye, but not the contralateral eye, suggesting the absence of systemic absorption. This reduction in pressure is also accomplished with the absence of such side-effects as irritation, influence on pupillary accommodation and affectation of outflow facility.

Included within the scope of this invention are the pharmaceutically acceptable acid addition salts of the R,R-stereoisomer. Such salts, which can be prepared by well known techniques, are exemplified by the hydrochloride, sulfate, maleate, tartrate and citrate.

The R,R-stereoisomer of this invention is physically characterized as having a hydrochloride salt which exists in two crystalline forms, one melting at about 133°–134° C., and the other melting at about 192°–193.5° C. The hydrochloride of the R,R-stereoisomer possesses an $[\alpha]_D26$ of about −30.6° (conc. 1% in ethanol). It may be prepared by stereoselective synthesis as disclosed in European Published Patent Application No. 9702 (Apr. 16, 1980) and the aforementioned parent applications.

The R,R-stereoisomer is preferably administered in the form of ophthalmic pharmaceutical compositions adapted for topical administration to the eye such as solutions, ointments or as a solid insert. Formulations of this compound may contain from 0.01 to 5% and especially 0.5 to 2% of medicament. As a unit dosage form, between 0.001 to 5.0 mg., preferably 0.005 to 2.0 mg., and most preferably 0.005 to 1.0 mg. of the compound is generally applied to the human eye. However, the amount to be applied will vary with the age of the patient and the severity of the glaucoma.

The pharmaceutical preparation which contains the R,R-stereoisomer may be conveniently admixed with a non-toxic pharmaceutical organic carrier, or with a non-toxic pharmaceutical inorganic carrier. Typical of pharmaceutically acceptable carriers are, for example, water; mixtures of water and water-miscible solvents, such as lower alkanols; vegetable oils; polyalkylene glycols; petroleum based jelly; ethyl cellulose; ethyl oleate; carboxymethylcellulose; polyvinylpyrrolidone; isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600; carbowaxes 1,000, 1,500, 4,000, 6,000 and 10,000; antibacterial components, such as quaternary ammonium compounds, phenylmercuric salts known to have cold sterilizing properties and which are non-injurious in use, thimerosal, methyl and propyl paraben, benzyl alcohol, phenyl ethanol; buffering ingredients such as sodium chloride, sodium borate, sodium acetates, gluconate buffers; and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid; and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert. For example, one may use a solid water soluble polymer as the carrier for the medicament. The polymer used to form the insert may be any water solule non-toxic polymer, for example, cellulose derivatives such as methylcellulose, sodium carboxymethyl cellulose, hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, agar, acacia; the starch derivatives such as starch acetate, hydroxyethyl starch ethers, hydroxypropyl starch, as well as other synthetic derivatives such as polyvinyl methyl ether, polyethylene oxide, neutralized carbopol and xanthan gum, and mixtures thereof.

Preferably the solid insert is prepared from cellulose derivatives such a methylcellulose, hydroxyethyl cellulose, hydroxpropyl cellulose or hydroxypropylmethyl cellulose or from other synthetic materials such as polyvinyl alcohol, polyvinyl pyrrolidone, polyethylene oxide or polyvinyl methylester. Hydroxypropyl cellulose, a preferred polymer for the preparation of the insert, is available in several polymeric forms, all of which are suitable in the preparation of these inserts. Typical hydroxypropyl celluloses which are suitable are those sold by Hercules, Inc. of Wilmington, Delaware under the name KLUCEL, such as KLUCEL HF, HWF, MF, GF, JF, LF and EF which are intended for food or pharmaceutical use. The molecular weight of these polymers useful for the purposes described herein is in the range of 30,000 to about 1,000,000 or more. Similarly, an ethylene oxide polymer having a molecular weight of up to 5,000,000 or greater, and preferably 100,000 to 5,000,000 can be employed. For example, POLYOX, a polymer supplied by Union Carbide Co. may be used having a molecular weight of about 50,000 to 5,000,000 and preferably 3,000,000 to 4,000,000 is useful in the present invention. Other specific polymers which are useful are those such as polyvinyl pyrrolidine having a molecular weight of from about 10,000 to about 1,000,000 or more, and most preferably about 20,000 to 60,000; polyvinyl alcohol having a molecular weight of from about 30,000 to 1,000,000 or more, particularly from about 100,000 to about 200,000; hydroxypropylmethyl cellulose having a molecular weight of from about 10,000 to 1,000,000 or more, particularly about 80,000 to about 125,000; methyl cellulose having a molecular weight of from about 10,000 to about 1,000,000 or more, and most preferably about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymer can be used having an average molecular weight which will afford dissolution of the polymer and the medicament over the desired length of time. The inserts can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively, the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye. The insert can be of any suitable size to readily fit into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates or ovals. Similarly, extruded rods having a diameter between about 0.5 and 1.5 mm. can be cut into suitable sections to provide the desired amount of polymer. The inserts may also be directly formed by injection molding. It is preferred that the ophthalmic inserts containing the medicament of the present invention be formed so that they are smooth and do not have any sharp edges or corners which could cause damage to the eye. By this is meant that excessive irritation of the eye will not result from the use of the insert.

The ocular medicinal inserts may also contain plasticizers, buffering agents and preservatives. Plasticizers suitable for this purpose must, of course, also be completely soluble in the lacrimal fluids of the eye. Examples of suitable plasticizers are water, polyethylene glycol, propylene glycol, glycerine, trimethylol propane, di- and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least 5% up to about 40%. A water content of from about 10% to about 20% is preferred since it may be easily accomplished and adds the desired softness and pliability to the insert.

When plasticizing the solid medicinal product with water, the product is contacted with air having a relative humidity of at least about 5% water so as to make it softer and more pliable. In a preferred embodiment, the relative humidity of the air is from about 60% to about 99% and the contacting is continued until the water is present in the product in amounts from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and most preferably are present in an amount of about 0.1 to 2%.

Suitable water soluble buffering agents are alkali, alkali earth carbonates, phosphates, bicarbonates, citrates, borate, acetate, bicarbonate and carbonate. These agents may be present in amounts sufficient to obtain a pH of the system of between 5.5 to 8.0 and especially 7-8; usually up to about 2% by weight of polymer. The insert may contain from about 1 mg. to 10 mg. of water soluble polymer, more particularly from 5 to 20 mg. The medicament is present from about 0.1 to about 25% by weight of insert.

The following examples describe in detail the preparation of compositions useful in the method of the present invention. It will be apparent to those skilled in the art that many modifications, both of materials and methods, may be practiced without departing from the purpose and intent of this disclosure.

In the following examples, the active ingredient is preferably (−)-5-{(R)-1-hydroxy-2-[(R)-(1-methyl-3-phenylpropyl)-amino]ethyl}salicylamide hydrochloride, but an equivalent quantity of the (R,R)-stereoisomer itself or of another pharamaceutically acceptable acid addition salt, especially a salt named herein, may be substituted:

EXAMPLE 1

| Ophthalmic Solution Composition | | |
|---|---|---|
| Active ingredient | 1 mg | 15 mg |
| Sodium phosphate monobasic . 2H$_2$O | 9.38 mg | 6.10 mg |
| Dibasic sodium phosphate . 12H$_2$O | 28.48 mg | 16.80 mg |
| Benzalkonium chloride | 0.10 mg | 0.10 mg |
| Sodium hydroxide q.s. | pH 6.8 | pH 6.8 |
| Water for injection q.s. ad. | 1.0 ml | 1.0 ml |

The active ingredient, phosphate buffer salts, and benzalkonium chloride are added to and dissolved in water. The pH of the solution is adjusted to 6.8 with sodium hydroxide and the final solution diluted to volume. The solution is rendered sterile by filtration through a sterilizing filter.

EXAMPLE 2

| Ophthalmic Ointment Composition | |
|---|---|
| Active ingredient | 5 mg |
| Petrolatum q.s. ad. | 1 gm |

The active ingredient and the petrolatum are aseptically combined.

EXAMPLE 3

| Ophthalmic Insert | |
|---|---|
| Active ingredient | 1 mg |
| Hydroxypropylcellulose q.s. | 12 mg |

Ophthalmic inserts are manufactured from compression molded films which are prepared on a Carver Press by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for ½ hour.

What is claimed is:

1. A method for treating glaucoma and for lowering intraocular pressure which comprises topically applying to the glaucomatous eye an intraocular pressure lowering effective amount of (−)-5-{(R)-1-hydroxy-2-[(R)-1-methyl-3-phenylpropyl)-amino]ethyl}salicylamide or a pharmaceutically acceptable salt thereof, substantially free from its stereoisomers, together with a vehicle suitable for ophthalmic use.

2. A method according to claim 1 wherein the (−)-5-{(R)-1-hydroxy-2-[(R)-1-methyl-3-phenyproply)amino]ethyl}salicylamide or a pharmaceutically acceptable salt thereof is administered as a 0.01 to 5% solution of (−)-5-{(R)-1-hydroxy-2-[(R)-1-methyl-3-phenylpropyl)amino]ethyl}salicylamide in an ophthalmologically acceptable carrier.

3. A method according to claim 1 wherein the (−)-5-{(R)-1-hydroxy-2-[(R)-1-methyl-3-phenylpropyl-)amino]ethyl}-salicylamide or a pharmaceutically acceptable salt thereof is administered in a water soluble polymeric insert.

4. A method according to claim 1 which comprises topically applying to the glaucomatous eye an intraocular pressure lowering effective amount of (−)-5-{(R)-1-hydroxy-2-[(R)-1-methyl-3-phenylpropyl)amino]ethyl}salicylamide, substantially free from its stereoisomers, together with a vehicle suitable for ophthalmic use.

* * * * *